(12) United States Patent
Wong

(10) Patent No.: US 6,818,452 B2
(45) Date of Patent: Nov. 16, 2004

(54) LATERAL FLOW CONTACT TEST APPARATUS

(75) Inventor: Raphael C. Wong, Irvine, CA (US)

(73) Assignee: Branan Medical Corp., Irvine, CA (US)

(*) Notice: Subject to any disclaimer, the term of this patent is extended or adjusted under 35 U.S.C. 154(b) by 0 days.

(21) Appl. No.: 09/840,566

(22) Filed: Apr. 23, 2001

(65) Prior Publication Data

US 2002/0155028 A1 Oct. 24, 2002

(51) Int. Cl.[7] .............................................. G01N 33/48
(52) U.S. Cl. ..................... 436/169; 436/135; 436/128; 436/816; 436/901; 422/58; 422/61
(58) Field of Search ............... 422/58, 61; 436/164, 436/169, 815–816, 901, 63, 128, 135

(56) References Cited

U.S. PATENT DOCUMENTS

| | | | | |
|---|---|---|---|---|
| 5,006,474 A | * | 4/1991 | Horstman et al. | 436/524 |
| 5,824,554 A | * | 10/1998 | McKay | 116/201 |
| 5,916,815 A | * | 6/1999 | Lappe | 436/92 |
| 6,203,757 B1 | * | 3/2001 | Lu et al. | 422/58 |
| 6,503,726 B2 | * | 1/2003 | Anne et al. | 435/28 |
| 6,514,769 B2 | * | 2/2003 | Lee | 436/518 |
| 6,689,618 B1 | * | 2/2004 | Chen | 436/135 |
| 2003/0039583 A1 | * | 2/2003 | Miller et al. | 422/58 |

\* cited by examiner

*Primary Examiner*—Lyle A. Alexander
(74) *Attorney, Agent, or Firm*—Myers Dawes Andras & Sherman LLP; Vic Lin

(57) ABSTRACT

A test strip assembly for detecting the presence of a substance in liquid sample comprises a contact detection pad in communication with a reagent-free absorbent strip. The absorbent strip receives the liquid sample and communicates it to the contact detection pad via lateral flow. The absorbent strip and contact detection pad are adhered to a support. A liquid impermeable pad is disposed adjacent to and spaced apart from the contact detection pad to prevent any further travel of the sample. Further add-on assemblies may be coupled to the base test strip assembly. The test strip assembly may be disposed in a housing along with a drug test strip to form a device that performs multiple types of tests. Methods for assaying and manufacturing are also provided.

32 Claims, 6 Drawing Sheets

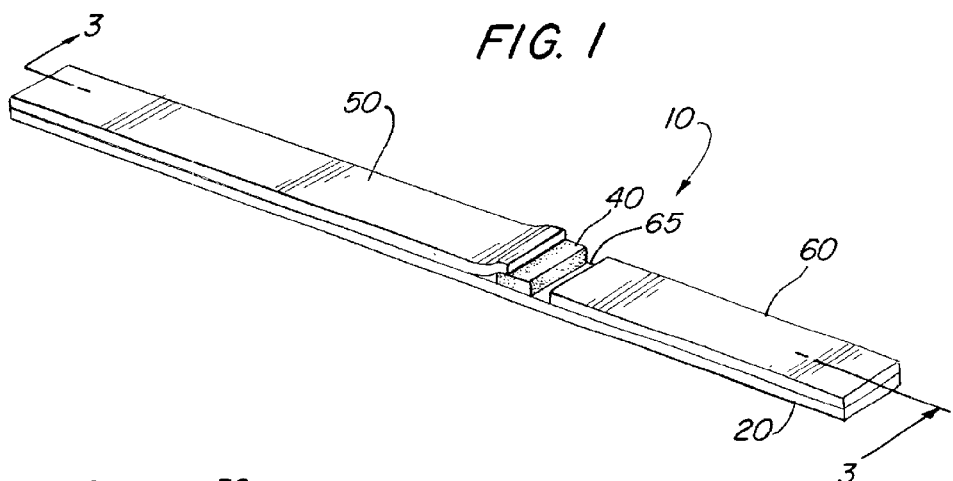
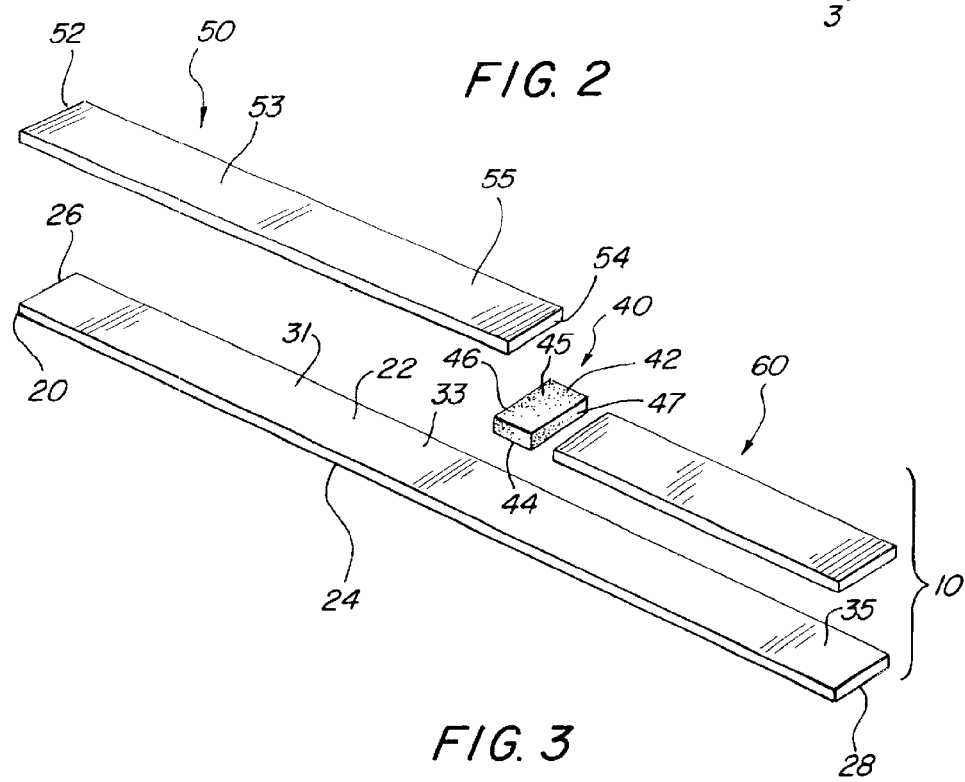
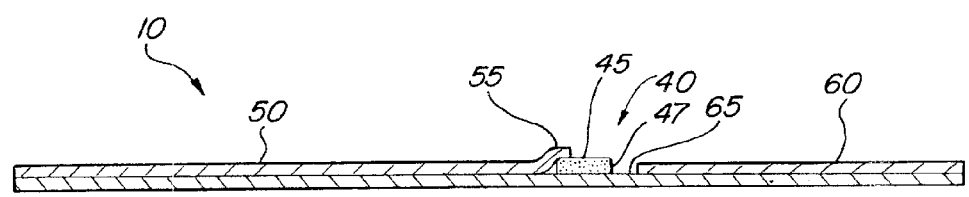

LATERAL FLOW CONTACT TEST APPARATUS

BACKGROUND OF THE INVENTION

1. Field of the Invention

The invention relates generally to urinalysis devices.

2. Description of Prior Art and Related Information

Chemical contact test devices generally include a test agent, such as a test pad containing one or more chemicals, adapted to come into contact with a fluid sample to be tested. Specific chemicals are provided in the test agent to react with the certain chemicals being detected in the fluid sample. If the chemicals being tested for are present in the sample, a chemical reaction occurs, resulting in a visible color change in the testing agent. By comparison with a color chart, the resulting color on a pad indicates whether certain chemicals are present. Such chemical "contact" tests include devices which may be used, for example, in urinalysis to aid in diagnosis and monitoring the progress of disease, to screen a population for asymptomatic, congenital or hereditary diseases, and to monitor the effectiveness or complications of therapy. In addition, it may be used to test for chemical adulteration of body fluids, such as urine.

As drug screening becomes increasingly prevalent, a greater need exists to detect adulterants used to thwart such drug tests. Adulterants, such as bleach for example, may interfere with the mechanism of the drug test, causing the test to report false results. A major problem with present drug screening, therefore, is the inaccuracy of a drug test due to the possible usage of adulterants.

Adulteration testing devices have been developed to address this uncertainty. Conventional adulteration testing devices include a dipstick containing several chemical contact test pads which is immersed into the fluid sample being tested. A major problem with conventional adulteration testing is that it consists of an additional test that must be performed with a device that is different and separate from the drug testing device. Hence, technicians are compelled to divide a liquid sample into multiple portions, increasing the probability of mix-ups and messy spills. A further disadvantage of the dipstick, as with other conventional urinalysis tests, is that once the fluid sample contacts the testing agent, chemicals from the testing agent may leach into the fluid sample. Thus, all of the fluid sample within a container is contaminated and rendered obsolete for further testing. If the fluid sample is not initially divided into separate containers, testing for adulteration may render the entire sample obsolete, thus requiring the donor to give a new sample and the technician to repeat testing.

In addition to drug testing and adulteration testing, the same contamination problem exists with current urinalysis in other types of applications, such as in the diagnosis of disease. Once a portion of a fluid sample contacts the testing agent, chemicals from the testing agent leach into that portion making it unusable for any further tests. This often leads to additional expense and inconvenience as the donor must resubmit a sample while additional materials and labor is required for retesting the new sample.

Furthermore, conventional urinalysis test devices include the dipstick which indicate the presence of certain substances, such as glucose or blood. In addition to the contamination problem, a conventional dipstick requires a large volume of urine held in a container of sufficient depth to allow a necessary length of the stick to be immersed. If a particular sample from a donor is small, testing the urine with a conventional urinalysis device may be precluded. Additional time, expense and inconvenience are incurred as the donor is compelled to resubmit a larger sample.

SUMMARY OF THE INVENTION

In one aspect, a lateral flow test strip assembly is provided for testing a liquid sample. The assembly comprises a support, a contact detection pad coupled to the support, and a reagent-free absorbent strip coupled to the support. As used in the specification and recited in the claims, the contact detection pad comprises an absorbent carrier and a reagent composition adapted to detect one or more substances which may be found in the liquid sample. Furthermore, as a "contact" detection pad, the reagent composition impregnated therein is adapted to detect such chemicals upon contact, as opposed to antibody-antigen binding associated with immunoassay strips. Thus, the reagent composition in the contact detection pad is not intended to be transported from one region of the pad to another region where a binding compound is disposed. The contact detection pad, therefore, excludes immunoassays, but comprises all other reagent compositions.

In a preferred embodiment, the contact detection pad comprises a contact urinalysis pad to detect one or more substances which may be found in urine. The contact urinalysis pad may comprise an adulteration pad to indicate whether a urine sample has been adulterated. The contact urinalysis pad may further comprise a bodily substance detection pad to detect bodily substances.

The reagent-free absorbent strip is in fluid communication with the contact urinalysis pad and is adapted to receive the urine and to communicate the urine to the contact urinalysis pad. As distinguished from immunoassays, the absorbent strip does not contain any antigens, antibodies, or any other reagents for that matter. Thus, the "reagent-free" absorbent strip primarily serves to direct the urine sample from a front, receiving portion to a rear end portion, where the urine is then communicated to the contact urinalysis pad.

The assembly further comprises means for preventing the urine from traveling beyond the contact urinalysis pad. The preventing means preferably comprises a liquid impervious pad coupled to the support. The liquid impervious pad is disposed adjacent to the contact urinalysis pad at the opposite end from the absorbent strip. The preventing means further comprises a gap between the contact urinalysis pad and the liquid impervious pad.

In a preferred embodiment, the absorbent strip is in fluid communication with the contact urinalysis pad. More particularly, the absorbent strip directly contacts and overlaps a portion of the contact urinalysis pad. The contact urinalysis pad may comprise an adulteration pad. The contact urinalysis pad may also comprise a bodily substance detection pad that detects for bodily substances other than antigens or antibodies.

In another aspect, a chemical test system is provided and adapted to test for the presence of multiple chemicals in a liquid sample. This multi-test system comprises a first sub-assembly and a second sub-assembly. The first sub-assembly, or base assembly, comprises a first backing, a first contact detection pad coupled to the first backing, and a first absorbent strip coupled to the first backing. The first contact detection pad includes an absorbent carrier and a reagent composition adapted to chemically react with a first chemical. The first absorbent strip is in communication with the first contact detection pad. The second sub-assembly, or add-on assembly, comprises a second absorbent strip in communication with the first absorbent strip, a second contact detection pad in communication with the second absorbent strip, and a second backing disposed between the second contact detection pad and the first absorbent strip.

The multi-test system further comprises a first liquid impervious pad coupled to the first backing and disposed adjacent to the first contact detection pad opposite to the first absorbent strip. The first liquid impervious pad is spaced apart from the first contact detection pad. The multi-test assembly further comprises a second liquid impervious pad coupled to the second backing and disposed adjacent to the second contact detection pad opposite to the second absorbent strip. The second liquid impervious pad is spaced apart from the second contact detection pad.

In a preferred embodiment, at least a portion of the first contact detection pad and at least a portion of the second contact detection are exposed. The first contact detection pad preferably comprises a first urinalysis pad. The second contact detection pad preferably comprises a second urinalysis pad.

In a further aspect, a chemical testing device is provided. The device comprises a housing, a contact urinalysis pad including a reagent composition adapted to react with one or more specific chemicals upon contact, and an absorbent strip in communication with the contact urinalysis pad. The housing includes means for viewing at least a portion of the contact urinalysis pad. In a preferred embodiment, the housing comprises a cassette. The housing comprises an aperture open to at least a portion of the absorbent strip. The device further comprises a lateral flow immunoassay strip disposed substantially within the housing.

In another preferred embodiment, the housing comprises a lid adapted to be removably coupled to a vessel. The device further comprises means for introducing a liquid sample in the vessel to the absorbent strip. The contact urinalysis pad preferably comprises an adulteration pad or a bodily substance detection pad. The device further comprises a lateral flow immunoassay strip disposed substantially within the housing.

A method for performing urinalysis is also provided. The method comprises receiving the liquid sample with a reagent-free absorbent strip, providing an urinalysis pad with a composition dispersed therein and adapted to test for a target substance upon contact, laterally flowing the liquid sample to the urinalysis pad with the reagent-free absorbent strip, and providing a detectable response as a result of detection of the target substance. The method further comprises assaying for a immunological chemical with a lateral flow immunoassay strip and preventing the liquid sample from traveling beyond the urinalysis pad.

A method for manufacturing a combined drug testing and adulteration testing device is provided as well. The method comprises providing a housing, disposing a drug test strip in the housing, disposing in the housing a reagent-free absorbent strip in communication with a contact detection pad, and preventing fluid communication between the drug test strip, on the one hand, and the absorbent strip and the contact detection pad, on the other hand. The method further comprises providing a stop to prevent a sample liquid absorbed in the contact detection pad from traveling beyond the contact detection pad. Providing a housing comprises forming apertures open to the drug test strip and the absorbent strip.

In conclusion, a test strip assembly for detecting the presence of a substance in liquid sample comprises a contact detection pad in communication with a reagent-free absorbent strip. The absorbent strip receives the liquid sample and communicates it to the contact detection pad via lateral flow. The absorbent strip and contact detection pad are adhered to a support. A liquid impermeable pad is disposed adjacent to and spaced apart from the contact detection pad to prevent any further travel of the sample. Further add-on assemblies may be coupled to the base test strip assembly. The test strip assembly may be disposed in a housing along with a drug test strip to form a device that performs multiple types of tests. Methods for assaying and manufacturing are also provided.

The invention, now having been briefly summarized, may be better visualized by turning to the following drawings wherein like elements are referenced by like numerals.

BRIEF DESCRIPTION OF THE DRAWINGS

FIG. 1 is a perspective view of a test strip according to the invention;

FIG. 2 is an exploded view of the test strip of FIG. 1;

FIG. 3 is a cross-sectional view taken along lines 3—3 of FIG. 1;

Figure 4:
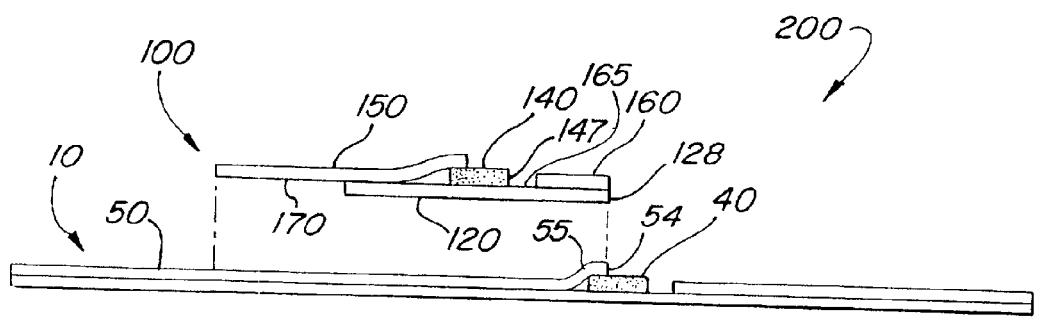
FIG. 4 is a partially exploded, side-view of a multi-test system according to the invention.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS

In FIGS. 1, 2 and 3, a first preferred embodiment of a lateral flow contact test assembly 10 is illustrated. The assembly 10 comprises a support, or backing, 20. The backing 20 has a supporting side, or surface, 22, an opposite resting side, or surface, 24, a front end 26 and a back end 28. The backing 20 comprises a front portion, 31, a midportion 33, and a rear portion 35.

A contact detection, or contact indicator, pad 40 is disposed on the midportion 33 of the backing 20 on the supporting side 22. A first surface 44 of the pad 40 is coupled to the backing 20. The contact detection pad 40 includes an outwardly facing second surface 45 opposite to the first surface 44, a front end 46, and a back end 47.

In a preferred embodiment, the contact detection pad 40 comprises a contact urinalysis pad 40 having an absorbent carrier 42 with a reagent composition disposed therein. The reagent composition is reactive with a certain chemical or chemicals which may be found in urine. The contact urinalysis pad 40 may comprise an adulteration pad having a reagent composition or compositions to indicate whether a liquid sample has been adulterated. The adulteration pad may provide such an indication by detecting certain adulterants which are not normal constituents of urine, such as bleach or glutaraldehyde, or by detecting an abnormal presence of a normal constituent of urine, such as creatinine.

The contact urinalysis pad 40 may also comprise a bodily substance detection pad having a reagent composition or compositions to detect bodily substances other than antigens or antibodies, such as glucose, bilirubin, ketone, blood, protein, urobilinogen, nitrite, leucocytes and more. The bodily substance detection pad may also measure pH and specific gravity of the urine.

The contact detection pad 40 is to be distinguished from conventional immunoassays which include colored antigens or antibodies disposed adjacent to a receiving end of a strip. In one such conventional immunoassay, the colored antigens along with any other antigens in the sample diffuse up the strip and react with a line of antibodies immobilized on the strip. If no antigens are present in the sample, the colored antigens are captured by the predisposed lines of antibodies on the strip, yielding a colored line which indicates a negative result. If antigens are present in the sample, such antigens are captured by the antibodies. This prevents the colored antigens from being captured by the antibodies, thus leaving the line colorless to indicate a positive result.

In contrast, the contact detection pad 40 according to the invention does not include antibodies intended to bind with antigens. Furthermore, the contact detection pad 40 is not a lateral flow strip in that it does not include predisposed chemicals designed to be carried along the pad, by a wicking liquid sample, from one region to another region where it may bind with an immobilized, second reagent composition. Instead, the reagent composition in the contact detection pad 40 provides a detectable response simply upon contact with the liquid sample if a certain substance is present. It is to be expressly understood that the contact detection pad 40 may be provided to detect substances in any liquid sample in addition to urine. Therefore, even though the contact detection pad 40 comprises a contact urinalysis pad in a preferred embodiment, the contact detection pad 40 is not limited to detecting substances in urine alone.

As discussed further below, the liquid sample is brought into contact with urinalysis pad 40 by a reagent-free absorbent strip 50. The absorbent strip 50 is disposed in fluid communication with the contact urinalysis pad 40. The absorbent strip 50 preferably contacts the urinalysis pad 40 directly such that the liquid sample wicking through the absorbent strip 50 is conveyed, or communicated, to the urinalysis pad 40. It is to be understood that one or more intermediary, reagent-free absorbent carriers may be disposed in between the absorbent strip 50 and the urinalysis pad 40 while still maintaining fluid communication therebetween. Therefore, the absorbent strip 50 may be in fluid communication with the urinalysis pad 40 whether or not the absorbent 50 directly contacts the urinalysis pad 40.

In a preferred embodiment, the absorbent strip 50 is coupled to the backing 20 and disposed over its front portion 31 and midportion 33. The absorbent strip 50 has a front end 52, a front receiving portion 53 adjacent thereto, a back end 54 and an adjacent rear portion 55. The absorbent strip 50 is thus adapted to receive a liquid sample at its receiving portion 53 and to convey the liquid sample from the receiving portion 53 to the rear portion 55 via capillary action.

The rear portion 55 of the absorbent strip 50 directly contacts the urinalysis pad 40 as shown in FIG. 3. Thus, the absorbent strip 50 is preferably disposed over a portion of the outwardly facing surface 45 in order to better facilitate fluid communication between the absorbent strip 50 and the contact urinalysis pad 40. The rear portion 55 of the absorbent strip 50 overlaps only a front portion of the contact urinalysis pad 40 such that the uncovered portion of outwardly facing surface 45 is visible.

The absorbent strip 50 is distinguished from those in immunoassays in that it does not contain any antigens, antibodies, or any other reagents for that matter. Thus, the "reagent-free" absorbent strip 50 primarily serves to direct the urine sample from the front, receiving portion 53 to a rear end portion 55, where the liquid sample is then communicated to the contact detection pad 40.

In FIGS. 1, 2 and 3, a liquid impervious pad 60 is coupled to the rear portion 35 of the backing 20. The impervious pad 60 is thus disposed adjacent to the back end 47 of the contact urinalysis pad 40 and slightly spaced apart therefrom to form a gap 65. In FIG. 3, the impervious pad 60 and the gap 65 collectively form a stop to prevent the liquid sample absorbed in the contact urinalysis pad 40 from traveling any further beyond the rear 47 of the urinalysis pad 40. In the case of a positive test result which yields a specific color in the urinalysis pad 40, this stop also serves to prevent the coloration of the contact urinalysis pad 40 from diffusing. It is to be understood that a variety of mechanisms may be employed to form the stop. For example, a hydrophobic line composed of wax or plastic may be disposed.

In the preferred embodiment, the absorbent strip 50, contact urinalysis pad 40, and the liquid impervious pad 60 are adhered to the support 20.

In operation, a liquid sample, such as urine, is introduced to the absorbent strip 50 at its receiving portion 53. Through capillary action, the liquid sample wicks through the absorbent strip towards the rear end 54. Thus, the absorbent strip 50 conveys the liquid sample from the receiving portion 53 to the rear portion 55 where the liquid sample is then communicated to the contact detection pad 40. The liquid sample is brought into contact with, and absorbed into, the contact detection pad 40. If a certain target substance, such as an adulterant or a specific bodily substance, is present in the liquid sample, a chemical reaction occurs between the chemical in the liquid sample and the predisposed chemical or chemicals in the contact detection pad 40. Thus, a chemical reaction results from the contact of the liquid sample with the contact detection pad 40, which contact is accomplished by the lateral capillary flow provided by the reagent-free absorbent strip 50.

In the field of urinalysis, it will be appreciated that what was once a device-to-sample test (i.e., the test device, such as a dipstick, had to be brought to the liquid sample) has been reversed in direction, i.e., sample-to-device (i.e., the liquid sample is brought to the device). One advantage of this reversal in direction is that the reagent composition in the urinalysis pad 40 will not leach out and contaminate any remaining liquid sample since the only portion affected will be the small amount introduced to the assembly 10. Thus, if the remaining urine is stored in a separate container or in a separate compartment of the same container, as will be shown below in a preferred embodiment, such remainder will remain unaffected and available for further testing. This conveniently obviates the need for any additional samples from the donor by preventing contamination of the remaining, untested urine.

A further advantage of the test strip assembly 10 is that only a small amount of urine is necessary for testing. Unlike the dipstick which must be immersed in a substantial volume of liquid sample, only a few simple drops of urine are required by the present assembly for testing. This minimizes inconvenience and embarrassment for the donor who may only be able to submit a small sample. Having to deal with only a few droplets of urine instead of a large volume also reduces exposure to the technician and facilitates improved sanitation.

Figure 5:
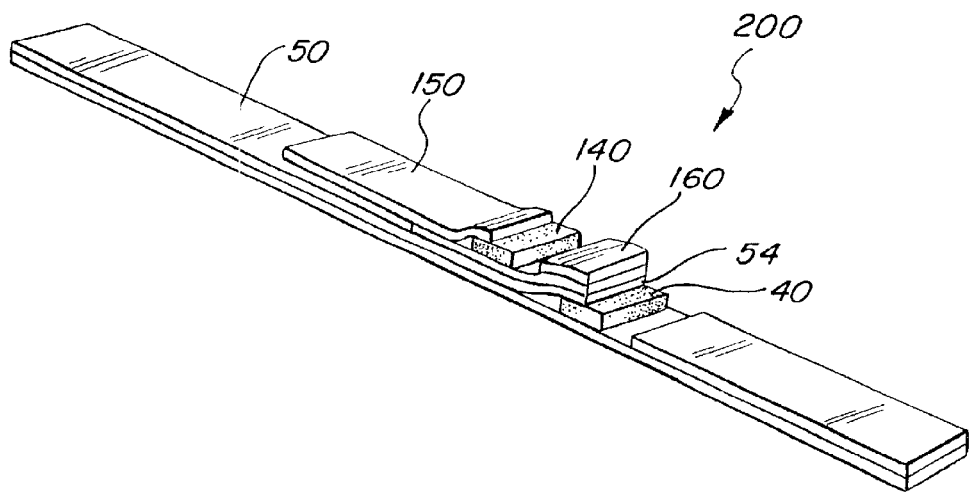
FIG. 5 is a perspective view of the multi-test system of FIG. 4.

It will further be appreciated that what was once a "contact" only test has been transformed to a lateral flow test, one advantage of which is that one or more assemblies may be coupled to a base assembly 10 to form a multi-test system 200 as shown in FIGS. 4 and 5. In the following description of the multi-test system 200, the term "first" generally refers to components of the base assembly 10 while the term "second" generally refers to components of the add-on assembly 100.

In FIGS. 4 and 5, the strip assembly 10 of FIGS. 1–3 serves as the base strip assembly to which a second strip assembly 100 is coupled. The second strip assembly 100 comprises a second reagent-free absorbent strip 150 that is in fluid communication with the first reagent-free absorbent strip 50 of the base assembly 10. The second absorbent strip 150 is coupled to a second backing 120. The second backing 120 is substantially shorter than the first backing 20 of the base assembly 10. The second backing 120 is coupled to the first absorbent strip 50, preferably by adhesion with two-sided tape 170. A second contact detection pad 140 is coupled to the second backing 120.

The second contact detection pad 140 includes a composition preferably to test for the presence of a substance different than the substance being tested for by the base contact detection pad 40. It will be appreciated that countless combinations may be formed. For example, both contact detection pads 40, 140 may comprise adulteration pads, each testing for a different adulterant. Alternatively, both contact detection pads 40, 140 may comprise bodily substance detection pads with each pad detecting a different bodily substance. As a further example, one contact detection pad 40 may comprise an adulteration pad while the other contact detection pad 140 comprises a bodily substance detection pad. It will be appreciated that the number of combinations increases exponentially with each new add-on assembly.

Similar to the base assembly 10, the second absorbent strip 150 directly contacts the second contact detection pad 140 and, preferably, overlaps a front portion of the second contact detection pad 140, leaving the remaining portion thereof uncovered. A second liquid impervious pad 160 is coupled to the second backing 120. The second liquid impervious pad 160 is disposed adjacent to and spaced apart from a back end 147 of the second contact detection pad 140.

In a preferred embodiment, the back end 128 of the backing 120, which is also the rearmost end of the entire add-on assembly 100, is flush with the back end 54 of the first absorbent strip 50 so as to not obstruct visual access to the first contact detection pad 40. Alternatively, the back end 128 of the backing 120 may be disposed in front of the back end 54 of the first absorbent strip 50, but preferably not any further past the back end 54.

With the rear portion 55 of the first absorbent strip 50 covering a front portion of the top of the first urinalysis pad 40, it will be appreciated that the first absorbent strip 50 serves as both a support for the add-on assembly 100 as well as a shield for the first contact detection pad 40. A second gap 165 in conjunction with the second liquid impermeable pad 160 serve to prevent any liquid sample from traveling beyond the back end 147 of the second contact detection pad 140.

In operation, a liquid sample is introduced to the first absorbent strip 50 is communicated to the first contact detection pad 40 as previously described above. As the liquid sample is conveyed from the receiving portion 53 to the rear portion 55 of the first absorbent strip 50, the liquid sample is communicated to the second absorbent strip 150. In the add-on assembly 100, the liquid sample is communicated to the second contact detection pad 140. The second gap 165 and second liquid impervious pad 160 prevent the liquid sample from traveling beyond the back end 147 of the second contact detection pad 140.

The scalability of the present invention will be appreciated as further add-on assemblies may be provided with their corresponding absorbent strip in communication with the base absorbent strip 50 either directly or indirectly through an intermediary reagent-free absorbent strip or strips. An advantage of this lateral flow multi-test system 200 is that several tests may be performed with a single system that requires merely a few drops of urine.

A further advantage of the strip assembly 10 according to the invention is that it may be incorporated into a testing device that also assays for immunological chemicals, such as antigens and antibodies, to determine, for example, illegal drug use.

Figure 6:
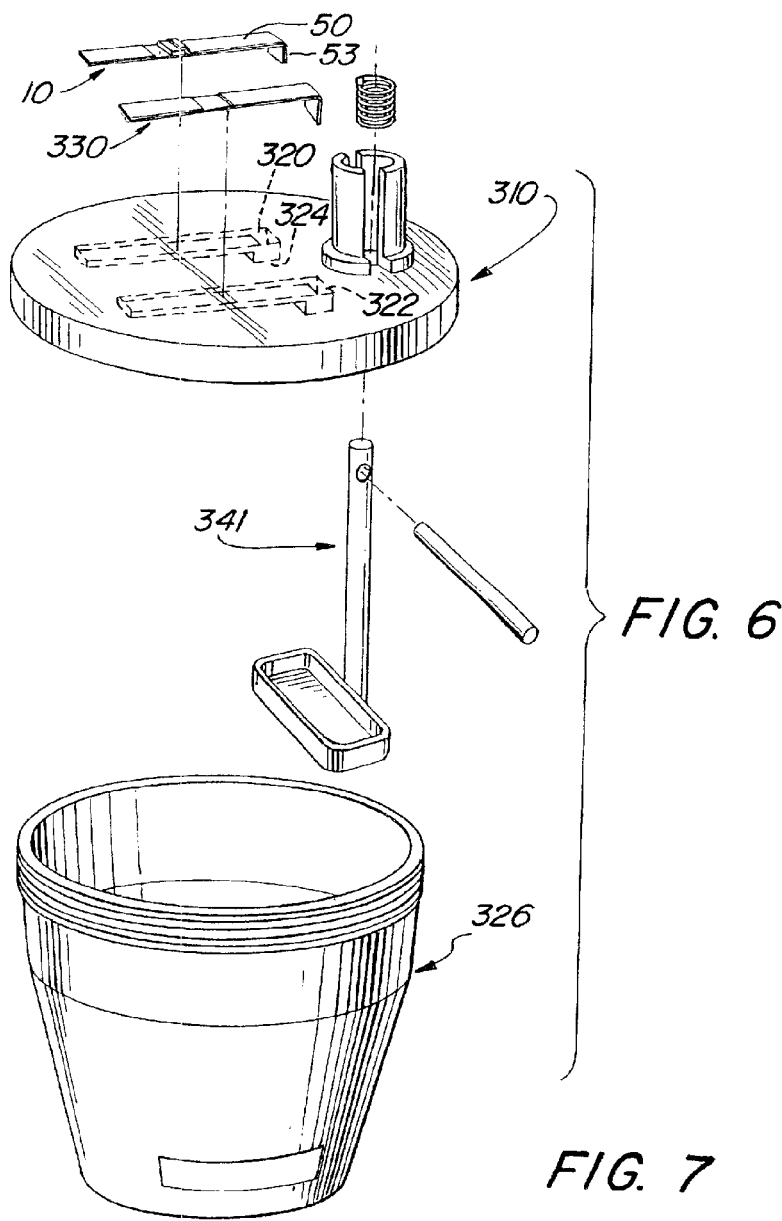
FIG. 6 is an exploded view of a preferred embodiment of a test device incorporating the test strip.
Figure 7:
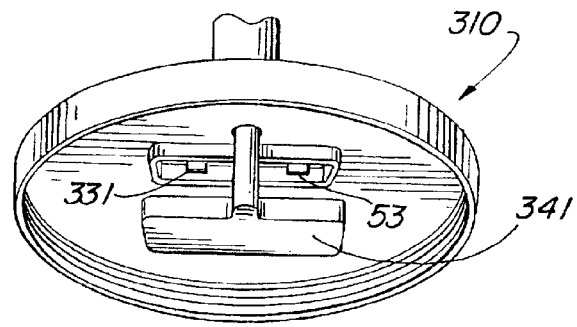
FIG. 7 is a perspective view of a removable lid of the test device of FIG. 6.

In FIGS. 6 and 7, the strip assembly 10 according to the invention may be disposed within a compartment of a housing 310. In a preferred embodiment, the housing 310 comprises a removable lid, or cap, adapted to be coupled to a vessel 326, such as a cup, for holding a liquid sample. The strip assembly 10 is disposed in a compartment 320 within the lid 310. The lid 310 further comprises a separate compartment 322 for holding a conventional drug test strip 330, such as a lateral flow immunoassay strip. The receiving portion 53 of the absorbent strip 50 is bent downward to exit a port 324 in the lid 310. Thus, the receiving portion 53 of the absorbent strip 50 along with a receiving portion 331 of the drug test strip 330 protrude downwardly through the lid 310 so as to receive the liquid sample carried thereto by the scoop 341.

It will be appreciated that both adulteration testing and drug testing is concurrently provided by a single device. The contact urinalysis pad 40 is disposed in the compartment 320 and is viewable through the translucent or transparent lid 310. Similarly, the drug test strip 330 is disposed in its corresponding compartment 322 and viewable through the lid 310. Thus, the juxtaposition of the adulteration strip assembly and the drug test strip 330 provides greater ease of use and viewing.

Figure 8:
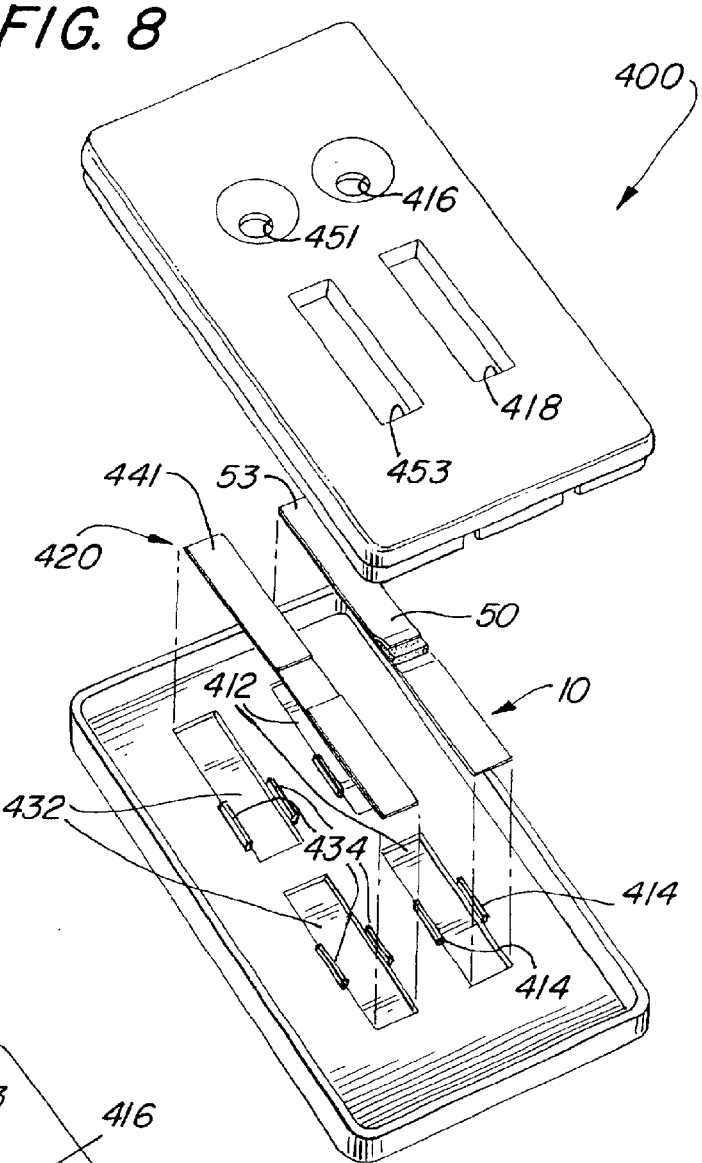
FIG. 8 is an exploded view of a further preferred embodiment of a test device incorporating the test strip.
Figure 9:
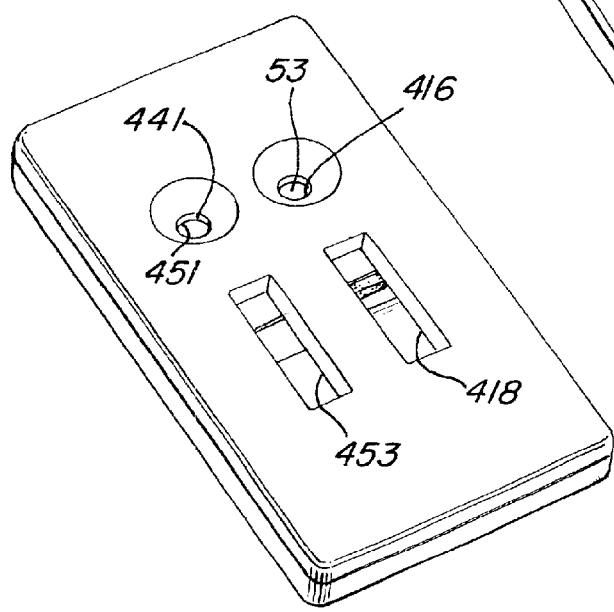
FIG. 9 is a perspective view of the test device of FIG. 8.

In an alternate preferred embodiment shown in FIGS. 8 and 9, the housing may comprise a cassette 400. The strip assembly 10 according to the invention may be disposed in the cassette 400 and retained by a first group of recesses 412 and projections 414. The receiving portion 53 of the absorbent strip 50 is disposed beneath a first receiving aperture 416 of the cassette 400 while the contact urinalysis pad 40 is disposed beneath an indicator aperture 418 of the cassette 400 such that the results are viewable. A drug test strip 420 is also disposed in the cassette 400 and retained by a second group of recesses 432 and projections 434. A receiving portion 441 of the drug test strip 420 is disposed beneath a second receiving aperture 451 while the indicator lines of the drug test strip 420 are disposed beneath a second indicator aperture 453.

As with the cap embodiment 300 shown in FIGS. 5 and 6, the drug test strip 420 is juxtaposed with the strip assembly 10 according to the invention in order to provide a convenient way of viewing both results. It will be appreciated that with the receiving apertures 416, 451 placed adjacent to each other, a technician may easily place drops of the liquid sample in both apertures 416, 451 in a single motion. As with the cap embodiment 300, the side-by-side arrangement of the strip assembly 10 according to the invention and the drug test strip 420 enables a technician to easily view results with a single glance, thus obviating the need in the prior art to look at separate devices.

Figure 10:
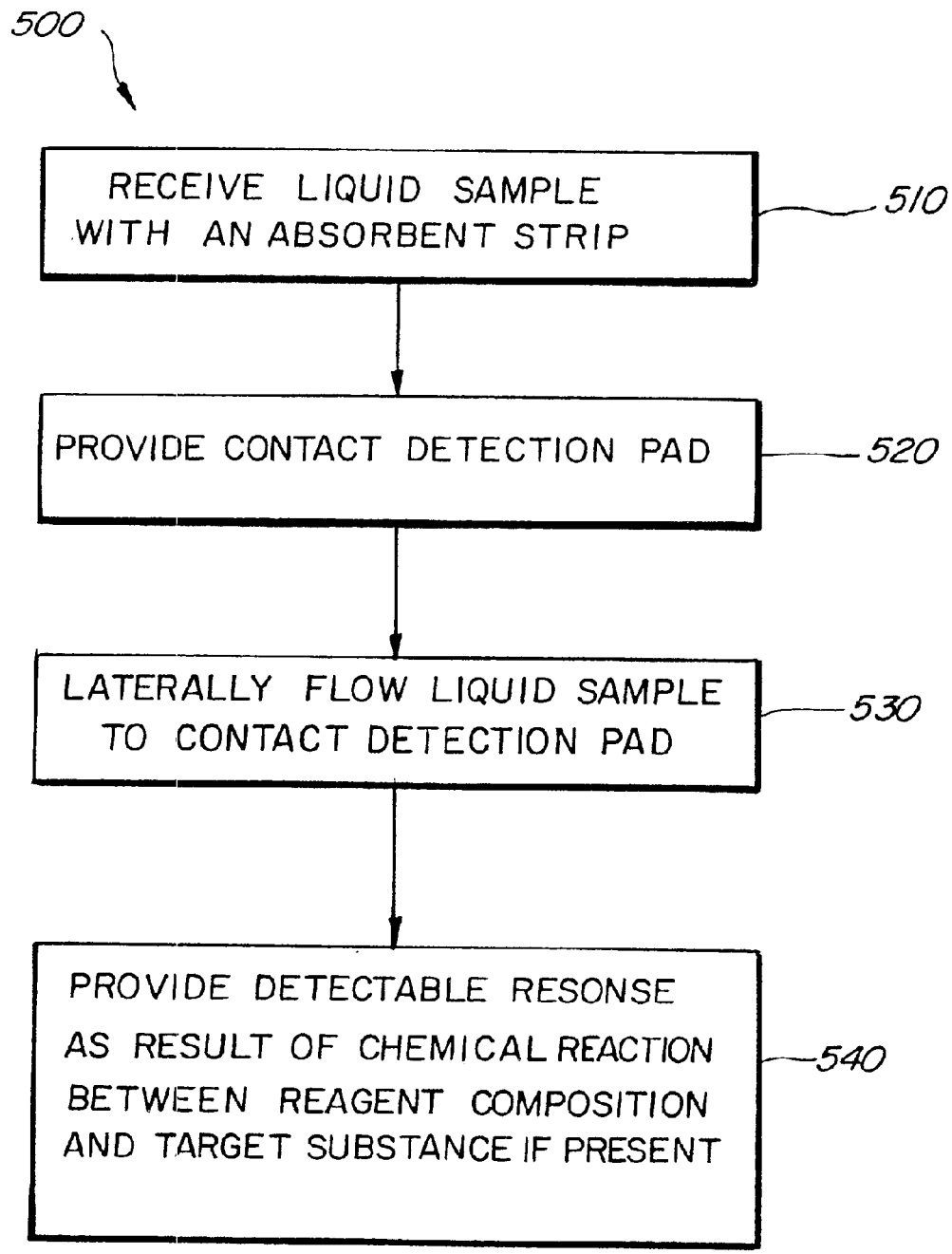
FIG. 10 is a flow diagram illustrating a preferred method of detecting a target substance in a liquid sample.

FIG. 10 is a flow diagram illustrating a preferred method 500 of assaying for a target substance or substances. A liquid sample is received with a reagent-free absorbent strip in step 510. Alternatively stated, the liquid sample is introduced to the absorbent strip, preferably, at a front receiving portion. In step 520, a contact detection pad is provided having dispersed therein a composition adapted to test for a substance upon contact. In step 530, the liquid sample is laterally flowed to contact the contact detection pad. The lateral flow is accomplished with the capillary action provided by the absorbent strip. If the target substance or substances to be detected are present in the liquid sample, a detectable responses is provided as result of a chemical reaction between the reagent composition and the substance or substances.

Figure 11:
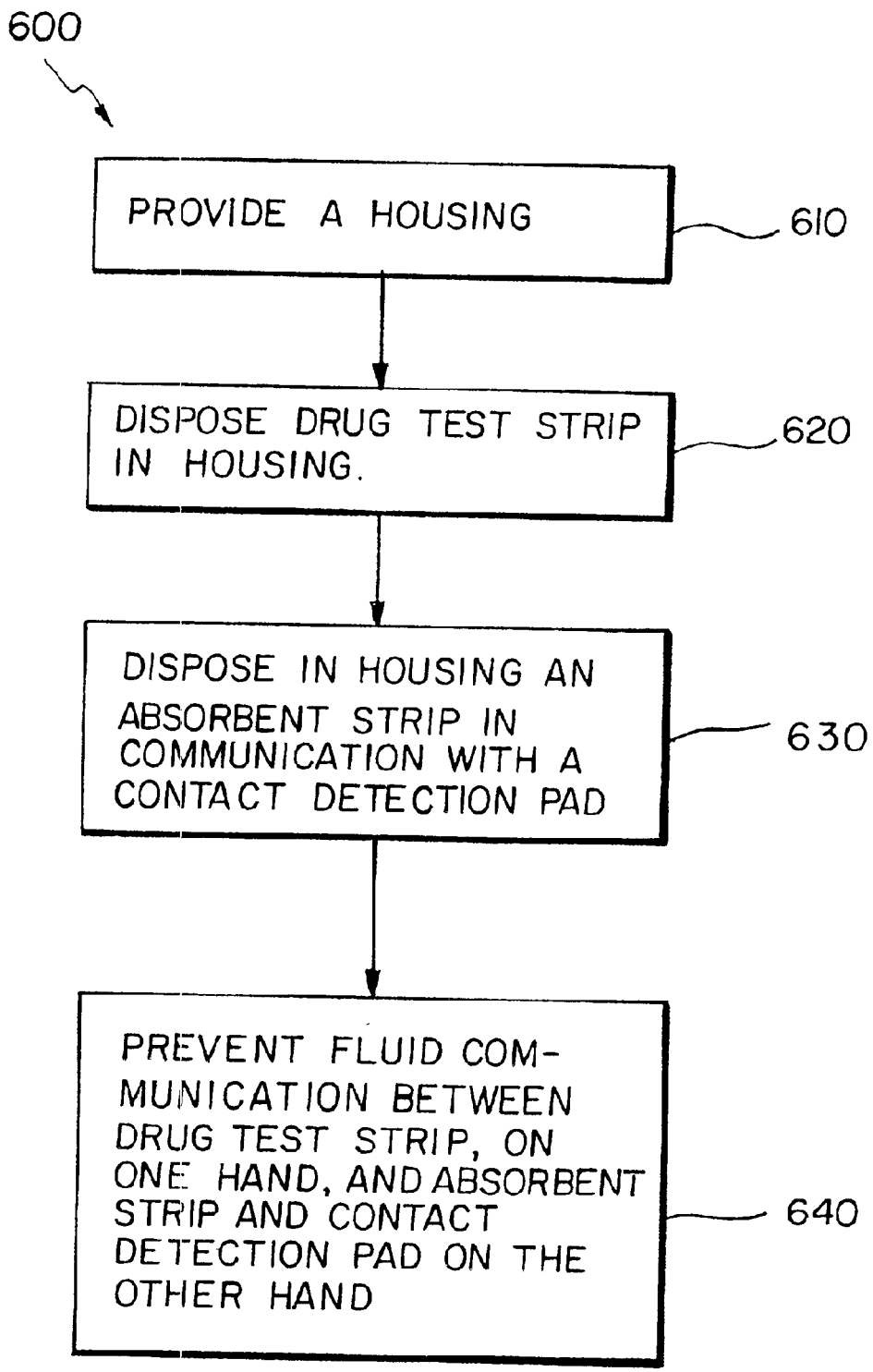
FIG. 11 is a flow diagram illustrating a preferred method of manufacturing a combined drug testing and contact detection pad device.

FIG. 11 is a flow diagram illustrating a method of manufacturing a combined drug testing and adulteration testing device. In step 610, a housing is provided. In a preferred method, the housing may be formed as a removable lid to a vessel, or as a cassette. In step 620, a drug test strip is disposed in the housing. The drug test strip preferably comprises a lateral flow immunoassay to test for the presence of illegal drugs. In step 630, a reagent-free absorbent strip and a contact detection pad are disposed in the housing and configured to be in communication with each other. The contact detection pad may include a contact urinalysis pad. This is preferably accomplished with the absorbent strip directly contacting the contact detection pad. Providing a housing includes forming apertures therein that are open to the drug test strip and the absorbent strip. In step 640, fluid communication is prevented between the drug test strip, on the one hand, and the absorbent strip and adulteration pad, on the other hand. This fluid isolation of each test preserves each respective test result by preventing any contamination therebetween.

It will be appreciated that according to a preferred method of manufacturing a combination testing device, a single apparatus is provided which can perform different tests, such as detecting illegal drugs, adulterants, bodily substances and more.

Many alterations and modifications may be made by those having ordinary skill in the art without departing from the spirit and scope of the invention. Therefore, it must be understood that the illustrated embodiments have been set forth only for the purposes of example and that it should not be taken as limiting the invention as defined by the following claims. The claims are thus to be understood to include what is specifically illustrated and described above, what is conceptionally equivalent, what can be obviously substituted and also what incorporates the essential idea of the invention.

What is claimed is:

1. A lateral flow test strip assembly for testing adulterants in urine, the assembly comprising:
   a support;
   a non-immunoassay contact urinalysis pad coupled to the support and composed of a first material, the contact urinalysis pad comprising an absorbent carrier and a reagent composition adapted to detect for one or more of the adulterants upon contact;
   a reagent-free absorbent strip coupled to the support and composed of a second material, the absorbent strip being in fluid communication with the contact urinalysis pad, the absorbent strip adapted to receive the urine and to communicate the urine to the contact urinalysis pad.

2. The assembly of claim 1, further comprising means for preventing the urine from traveling beyond the contact urinalysis pad.

3. The assembly of claim 2, wherein the preventing means comprises a liquid impervious pad coupled to the support, the liquid impervious pad being disposed adjacent to the contact urinalysis pad and opposite from the absorbent strip.

4. The assembly of claim 3, wherein the preventing means further comprises a gap between the contact urinalysis pad and the liquid impervious pad.

5. The assembly of claim 1, wherein the absorbent strip is coupled to the contact urinalysis pad.

6. The assembly of claim 5, wherein the absorbent strip overlaps a portion of the contact urinalysis pad.

7. The assembly of claim 1, wherein the contact urinalysis pad is configured to detect abnormal adulterants selected from the group consisting of bleach and glutaraldehyde.

8. The assembly of claim 1, wherein the contact urinalysis pad is configured to detect an abnormal presence of a normal urine constituent.

9. A chemical test assembly adapted to test for the presence of multiple substances in a liquid sample, the assembly comprising:

a first backing;
a first non-immunoassay contact detection pad coupled to the first backing and composed of a first material, the first contact detection pad including a first absorbent carrier and a first reagent composition adapted to detect a first adulterant;
a first absorbent strip coupled to the first backing and composed of a second material, the first absorbent strip in fluid communication with the first contact detection pad;
a second absorbent strip in fluid communication with the first absorbent strip, the second absorbent strip being composed of a third material;
a second non-immunoassay contact detection pad being separate from, but in fluid communication with, the second absorbent strip comprising a second absorbent carrier and a second reagent composition adapted to detect for second adulterant, the second absorbent carrier being composed of a fourth material; and
a second backing disposed between the second contact detection pad and the first absorbent strip.

10. The assembly of claim 9, further comprising a first liquid impervious pad coupled to the first backing and disposed adjacent to the first contact detection pad opposite to the first absorbent strip.

11. The assembly of claim 10, wherein the first liquid impervious pad is spaced apart from the first contact detection pad.

12. The assembly of claim 9, further comprising a second liquid impervious pad coupled to the second backing and disposed adjacent to the second contact detection pad opposite to the second absorbent strip.

13. The assembly of claim 12, wherein the second liquid impervious pad is spaced apart from the second contact detection pad.

14. The assembly of claim 9, wherein at least a portion of the first contact detection pad and at least a portion of the second contact detection pad are exposed.

15. The assembly of claim 9, wherein:
the second contact detection pad comprises a second absorbent carrier and a second reagent composition adapted to detect the second adulterant, the second adulterant being different from the first adulterant.

16. A chemical testing device comprising:
a housing;
a non-immunoassay contact detection pad including a reagent composition adapted to detect one or more specific adulterants upon contact, the non-immunoassay contact detection pad being composed of a first material;
a reagent-free absorbent strip being separate from, but in fluid communication with, the contact detection pad, the reagent-free absorbent strip being composed of a second material; and
a lateral flow immunoassay drug test strip disposed substantially within the housing, the lateral flow immunoassay not having any fluid communication with the reagent-free absorbent strip.

17. The device of claim 16, wherein the housing includes means for viewing at least a portion of the contact detection pad.

18. The device of claim 16, wherein the housing comprises a cassette.

19. The device of claim 18, wherein the housing comprises an aperture open to at least a portion of the absorbent strip.

20. The device of claim 16, wherein the housing comprises a lid adapted to be coupled to a vessel.

21. The device of claim 20, further comprising means for introducing a liquid sample in the vessel to the absorbent strip.

22. The device of claim 20, wherein the lid is removable.

23. A lateral flow assembly for detecting adulterants in a liquid sample, the assembly comprising:
- a support;
- a non-immunoassay contact detection pad coupled to the support and composed of a first material, the contact urinalysis pad comprising an absorbent carrier and a reagent composition adapted to detect for one or more of the adulterants upon contact; and
- a reagent-free absorbent strip coupled to the support and composed of a second material, the absorbent strip in fluid communication with the contact detection pad, the absorbent strip overlapping at least a portion of the non-immunoassay contact detection pad so as to communicate the liquid sample to the contact detection pad.

24. The assembly of claim 23, wherein the contact urinalysis pad is configured to detect bleach.

25. The assembly of claim 23, wherein the contact urinalysis pad is configured to detect glutaraldehyde.

26. The assembly of claim 23, wherein the contact urinalysis pad is configured to detect an abnormal presence of a normal urine constituent.

27. A method for performing urinalysis, comprising:
- receiving the urine with a reagent-free absorbent strip;
- providing a separate non-immunoassy urinalysis pad with a reagent composition dispersed therein and adapted to detect a target adulterant upon contact;
- laterally flowing the urine to the urinalysis pad with the absorbent strip;
- providing a detectable response as a result of detection of the target adulterant.

28. The method of claim 27, further comprising assaying for an antigen with a lateral flow immunoassay strip.

29. The method of claim 27, further comprising preventing the urine from traveling beyond the urinalysis pad.

30. A method for manufacturing a combined drug testing and adulteration testing device, the method comprising:
- providing a housing;
- disposing a drug test strip in the housing;
- disposing in the housing a reagent-free absorbent strip composed of a first material in communication with a separate non-immunoassay contact detection pad that comprises an absorbent carrier composed of a second material and a reagent composition adapted to detect for one or more adulterants upon contact; and
- preventing fluid communication between the drug test strip and the absorbent strip and the contact detection pad.

31. The method of claim 30, further comprising providing a stop to prevent a liquid sample absorbed in the adulteration pad from traveling beyond the contact detection pad.

32. The method of claim 30, wherein providing a housing comprises forming apertures open to the drug test strip and the absorbent strip.

* * * * *